United States Patent [19]

Hokanson et al.

[11] Patent Number: 4,739,772

[45] Date of Patent: Apr. 26, 1988

[54] BRAIN WAVE MONITORING MECHANISM AND METHOD

[76] Inventors: D. Eugene Hokanson, 3324 - 72nd Ave. SE., Mercer Island, Wash. 98040; William M. Blackshear, Jr., 10106 Lindelaan, Tampa, Fla. 33618

[21] Appl. No.: 462,732

[22] Filed: Feb. 1, 1983

[51] Int. Cl.[4] .............................................. A61B 5/04
[52] U.S. Cl. .................................................. 128/731
[58] Field of Search ............................. 128/702–704, 128/710–712, 731

[56] References Cited

U.S. PATENT DOCUMENTS

| Re. 28,214 | 10/1974 | Maynard | 128/2.1 B |
| 3,613,669 | 10/1971 | Corbin et al. | 128/712 |
| 4,037,586 | 7/1977 | Grichnik | 128/731 |
| 4,098,267 | 7/1978 | Stein et al. | 128/712 |

FOREIGN PATENT DOCUMENTS 1247491 10/1968 United Kingdom .
1247492 10/1968 United Kingdom .

OTHER PUBLICATIONS

"EEG Processing by the Cerebral Function Monitor (CFM)", (Ann. Anesth. Franc., 3:170-174, 1979), by D. E. Maynard.
"General Anaesthesia and Changes on the Cerebral Function Monitor", (Anaesthesia 33:157-164, 1978), by Michel Dubois, T. M. Savege, T. M. O'Carroll and M. Frank.
"An Inexpensive Device for Analyzing and Monitoring the Electroencephalogram", (Anesthesiology 50:456-460, 1979), by Robert A. Fleming and N. Ty Smith.

Primary Examiner—William E. Kamm
Attorney, Agent, or Firm—Ward Brown; Robert W. Beach

[57] ABSTRACT

During a surgical operation, a conventional electroencephalograph provides several analog electrical signals of the brain waves of the patient, each signal indicating voltage fluctuations detected at a different area of the patient's scalp. The analog signals are converted to digital form for input to a multipurpose computer. The computer is programmed to produce respective reference traces on a video monitor indicating the voltage fluctuations detected during a preceding reference period. While the reference traces continue to be displayed, more current traces are produced on the video monitor in juxtaposed relationship to the reference traces. The current traces indicate the voltage fluctuations detected during the period immediately preceding their display. The current traces are replaced periodically with new current traces indicating more recent information. Any significant change in the patient's brain waves is detected by comparing the current traces with the reference traces. At predetermined times, the most recent current traces are recorded by encoding the corresponding digital signals on a disk. Later, the traces can be reproduced on the video monitor for postoperative evaluation.

14 Claims, 3 Drawing Sheets

BRAIN WAVE MONITORING MECHANISM AND METHOD

BACKGROUND OF THE INVENTION

1. Field of the Invention

The present invention relates to mechanism and a method for detecting the rhythmic voltage fluctuations or electrical signals generated in the brain and displaying such signals in viewable form, and also for storing such signals electronically so that they can be reproduced and displayed in viewable form at a desired time.

2. Prior Art

It has been proposed to monitor the brain waves or electrical brain activity of an anesthetized patient to indicate the depth or level of anesthesia, the object being to prevent too little or too much of the anesthetic agent from being administered to the patient. In addition, it is known that the level of electrical bran activity is affected by a substantial, sudden decrease in blood flow through the brain, and by a substantial decrease in oxygen supplied to the brain regardless of cerebral blood flow, which always are of concern while the patient is under the effect of an anesthetic agent. Accordingly, it has been proposed to continuously monitor the patient's electrical brain activity during a surgical operation and recovery.

The primary mechanism used to monitor electrical brain activity is the conventional electroencephalograph (EEG) which, unfortunately, has not proven to be practical for routine use in the operating or recovery room. In a conventional EEG, several, such as 16, electrodes attached to a patient's scalp detect the very small voltage fluctuations generated in the brain. The small voltage fluctuations are amplified and are separately displayed. Typically, 16 different EEG outputs are provided, each indicating the detected voltage difference between a selected pair of electrodes.

Interpretation of the many EEG outputs can require substanial study even by experienced EEG specialists which are expensive and in short supply. To allow time for this study, a permanent record of the EEG outputs is essential, which has been accomplished by use of a chart recorder having several pens deflected in response to the EEG ouputs and making tracings on a chart moved past the pens. So that the fluctuations are prominantly displayed on the chart, the chart is moved past the pens at fairly high speed, such as in the range of 15 mm to 60 mm per second. If the electrical brain activity is monitored over any substantial period, a voluminous and complicated paper record is generated.

Modified EEG-type devices have been proposed to overcome the expense and inconvenience of long-term brain wave monitoring by a conventional EEG. One such device is the "cerebral function monitor" described generally in an article titled "EEG Processing By The Cerebral Function Monitor (CFM)" (Ann. Anesth. Franc., 3:170-174, 1979) by the inventor of that device D. E. Maynard. The Maynard cerebral function monitor also is the subject of U.S. Pat. No. Re. 28,214 and British Pat. Nos. 1,247,491 and 1,247,492.

In general, the Maynard cerebral function monitor uses only two electrodes attached to the patient's scalp to detect the small voltage fluctuations generated in the brain. Only one electrical brain activity output signal is provided, with frequency components below about 2 hertz and above about 14 hertz filtered out. The remaining 2 hertz to 15 hertz signal is amplified, with the higher frequency components being amplified to a greater degree than the lower frequency components. The single filtered and amplified signal is displayed by use of a chart recorder, but the chart is moved at slow speed, such as several millimeters per minute, so that the pen oscillations are closely packed in a broad band. The top of the band indicates the maximum amplitude of electrical brain activity at a specific point in time and the bottom of the band indicates the minimum amplitude of the electrical brain activity at about the same time.

Initially Maynard proposed that his cerebral function monitor be used as a check on the validity of conventional EEG tracings taken intermittently over a long period. Various other uses for the cerebral function monitor have been suggested including its use as an indicator of the depth or level of anesthesia and to give a warning of a substantial, sudden decrease in cerebral blood flow which should be indicated by a corresponding decease in the amplitude of the cerebral function monitor output. See, for example, the article titled "General anaesthesia and changes on the cerebral function monitor" (Anaesthesia 33:157-164, 1978) by Michel Dubois, T. M. Savege, T. M. O'Carroll and M. Frank.

Other modified EEG-type devices are described in an article titled "An Inexpensive Device for Analyzing and Monitoring the Electroencephalogram" (Anesthesiology 50:456-460, 1979) by Robert A. Fleming and N. Ty Smith.

SUMMARY OF THE INVENTION

It is an object of the present invention to provide a novel mechanism and method for monitoring the electrical brain activity of a patient over a long period, such as during the couse of a surgical operation.

It also is an object to provide such mechanism and method for indicating in compact, viewable form both the amplitude and frequency of the patient's electrical brain activity.

Another object is too provide such mechanism and method for separately indicating the patient's electrical brain activity generated at a plurality of different areas of the brain.

An additional object is to provide such mechanism and method for indicating the patient's electrical brain activity in a form which does not require an experienced EEG specialist for useful evaluation.

A further object is to provide such mechanism in a form which is compact and easy to operate.

Still another object is to provide such mechanism and method for storing information indicating the patient's electrical brain activity and for reproducing such information in viewable form at a desired time.

These and other objects are accomplished by the brain wave monitoring mechanism and method of the present invention described below.

DETAILED DESCRIPTION OF THE PREFERRED EMBODIMENT

General Operation

Figure 1:
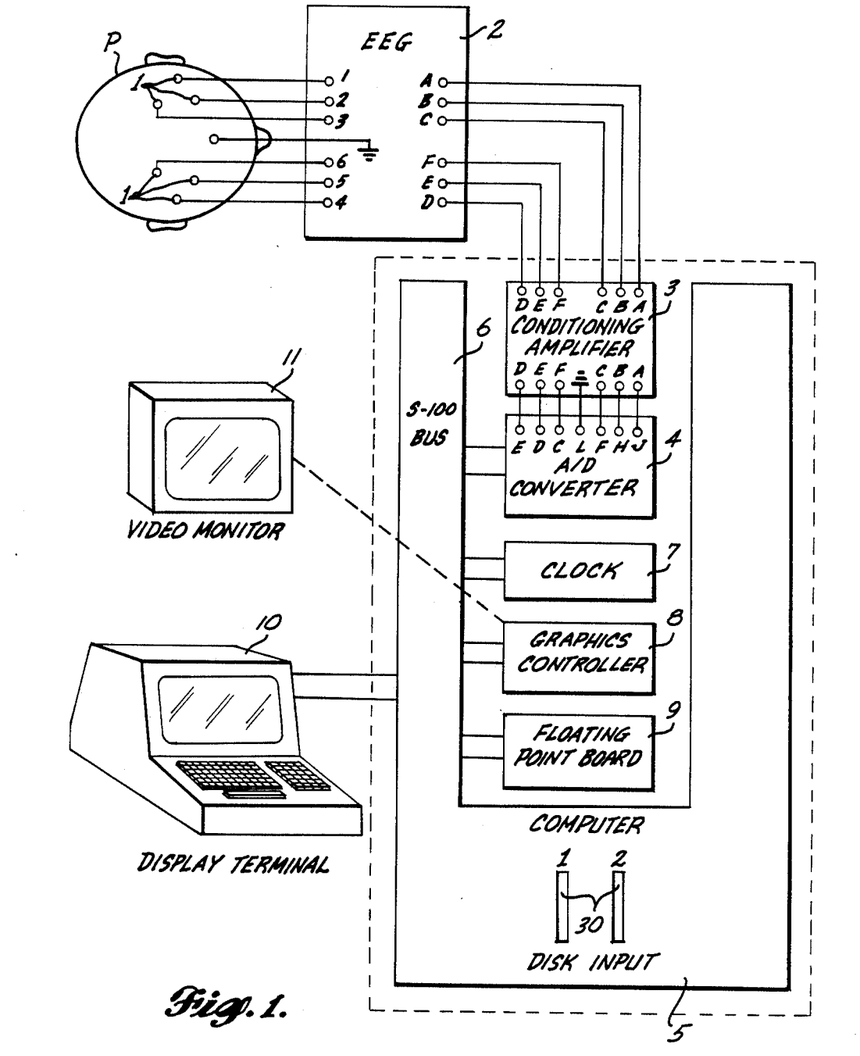
FIG. 1 is a block circuit diagram of the component parts of electrical brain wave monitoring mechanism in accordance with the present invention.

With reference to FIG. 1, six electrodes 1 of a conventional EEG 2 are attached to the scalp of a patient P, one set of three electrodes being attached at spaced locations at each side of the scalp. The ground electrode 1' of the EEG is attached to the patient's scalp at any convenient location such as the forehead.

For each set of three electrodes, the conventional EEG detects the voltage difference between each of the three possible combinations of two electrodes, filters out frequency components detected by the electrodes above about 15 hertz, amplifies the remaining signals and provides a separate, variable voltage output indicating the voltage difference between such two electrodes. Accordingly, the conventional EEG provides six variable voltage outputs.

In the present invention, the amplitudes of the output signals of the EEG are reduced uniformly by a conditioning or negative gain amplifier 3 which also offsets each signal uniformly to be in the positive range.

An analog-to-digital (A/D) convertor 4 converts the output signals of the conditioning amplifier from continuous variable voltage form to a digital signal conveying the same information for input to a multipurpose computer 5 having a standard bus 6 for connection of other accessories. Such accessories include a clock circuit 7, a graphics controller circuit 8, a floating point board circuit 9 and an operating terminal 10 having both keyboard and video display. A video monitor 11 is connected to the graphics controller circuit 8.

Figure 3:
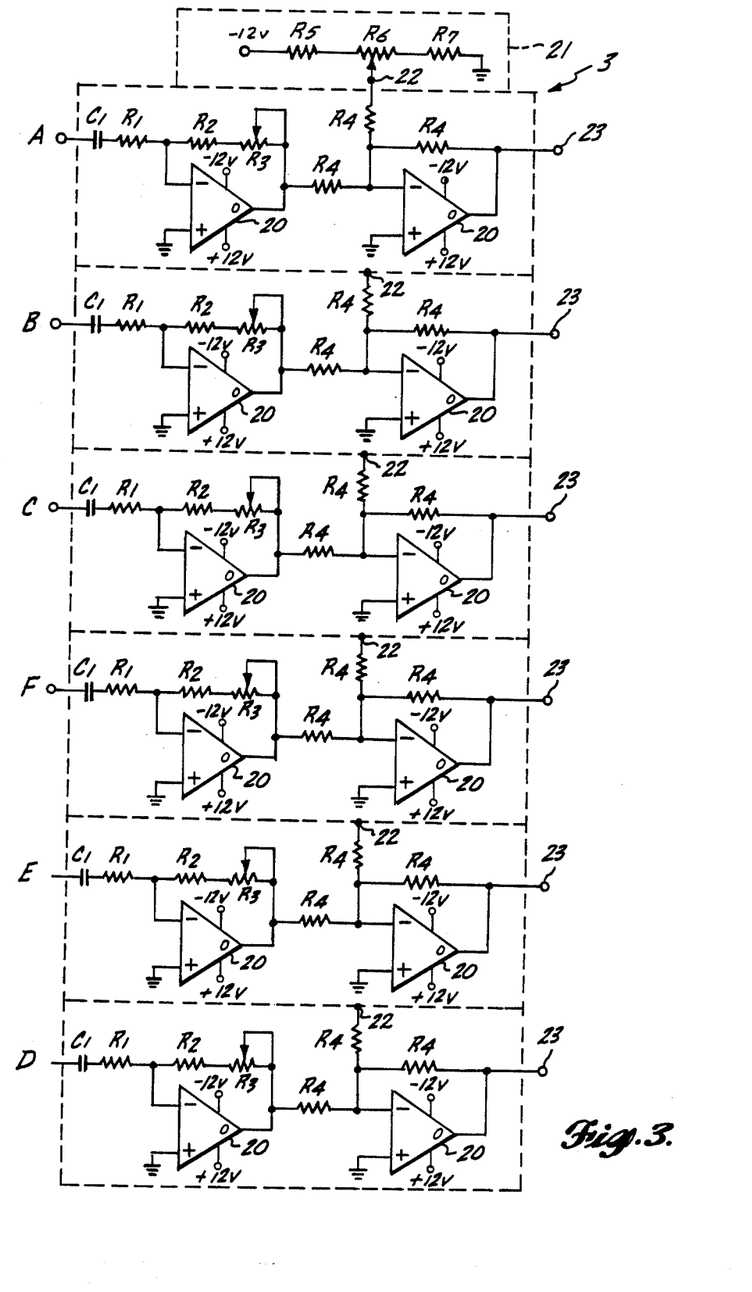
FIG. 3 is a circuit diagram of one component of the mechanism of FIG. 1.

All components of the electrical brain wave monitoring mechanism in accordance with the present invention are off-the-shelf items with the exception of the conditioning amplifier 3 for which the circuit diagram is shown in FIG. 3.

The computer is programmed to accept simple instructions by use of the keyboard of the operating terminal 10. Initially the computer receives and stores the digital output of the A/D convertor for a short period. As directed by the operator of the device through the keyboard of the terminal 10, these stored signals are displayed on the video monitor 11 as six horizontal, continuous traces, one for each of the electrodes 1. These traces extend substantially the full width of the video monitor in vertically spaced arrangement and are referred to as the "reference" or "high" traces which are shown as traces A, B, C, D, E and F on the video monitor as seen, for example, in FIGS. 4 through 7. The length of time represented by each full trace is referred to as the "scan time" which is within the range of about 1 second to about 30 seconds as preselected by the operator of the device.

Ideally, the reference traces indicate normal electrical brain activity of the particular patient at a desired time, such as at the beginning of a surgical operation. By selection of a longer scan time, each reference trace indicates electrical brain activity over a longer period than if a shorter scan time is selected, but the voltage fluctuations detected by the electrodes will appear more closely packed on the video monitor than if a shorter scan time were selected.

Figure 5:
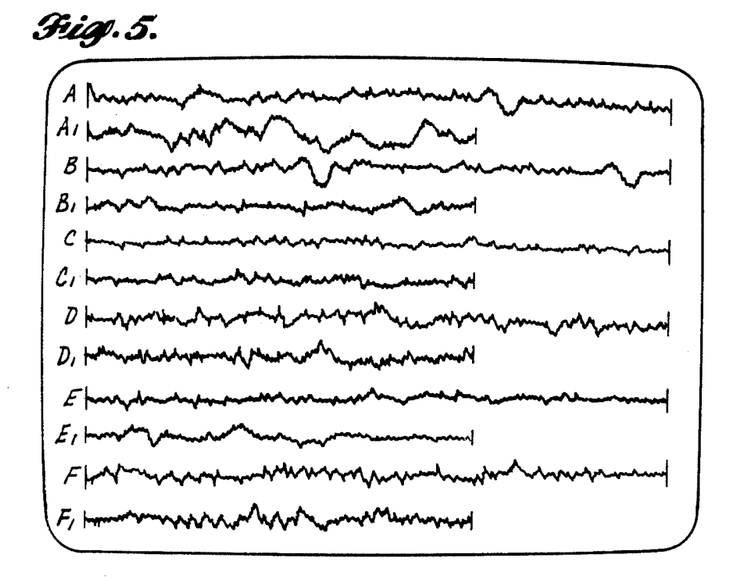
Figure 6:
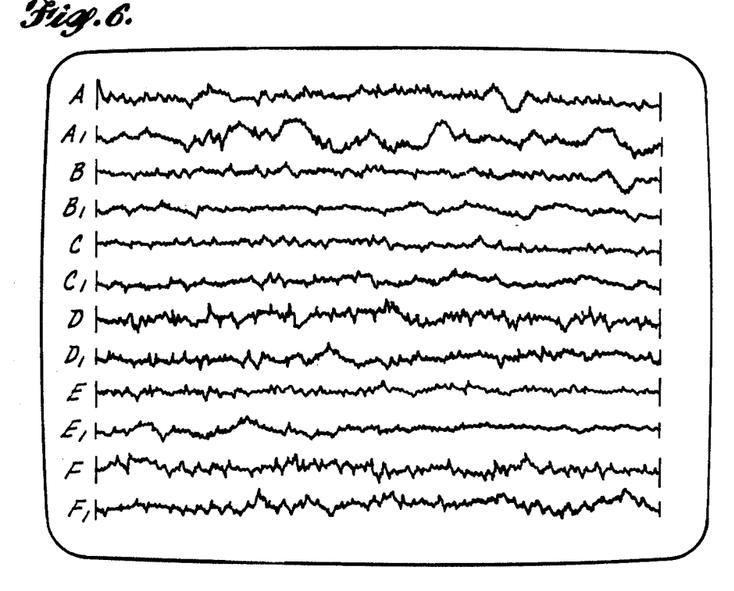

The reference traces continue to be displayed on the video monitor as the computer receives and stores the next segment of information from the A/D convertor for the preselected scan time. At the end of such scan time increment, the subsequent signals are displayed on the video monitor as quickly as possible after all of the information has been received. Each such subsequent signal is displayed as a separate trace beneath the corresponding previous reference trace. These subsequent signals ar referred to as the "live" traces, though they represent information gathered over the immediately preceding scan time increment. The live traces are indicated as traces $A_1$, $B_1$, $C_1$, $D_1$, $E_1$ and $F_1$ on the video monitor, as seen in FIGS. 5 and 6. FIG. 5 shows representative live traces as they are being generated on the video monitor from left to right and FIG. 6 shows the live traces after generation of a complete screen of information. Generation of the complete traces on the video monitor takes about two to five seconds.

Although the same reference traces continue to be displayed on the video monitor, each set of live traces is displayed only while the computer receives and stores the next segment of information for the preselected scan time, whereupon the prior live traces are replaced with new live traces showing the brain wave information detected during the scan time increment immediately preceding the displaying of the new traces. The process continues for as long as desired by the operator of the device during which such operator evaluates whether the live traces indicate normal brain activity as compared to the activity indicated by the reference traces. It is known, for example, that a marked decrease in the amplitude of electrical brain activity and, equally important, a substantial decrease in high frequency activity may indicate a decrease in cerebral blood flow. The reference traces shown in FIGS. 4 through 7 and the live traces shown in FIGS. 5 through 6 are representative of normal brain activity. The live traces $B_1$ and $C_1$ in FIG. 7, as compared to the corresponding reference traces B and C, show a substantial decrease in amplitude and are substantially smoother traces, indicating an absence of high frequency activity, such as would be expected if there had been a substantial decrease in cerebral blood flow in the areas of the corresponding electrodes. Upon viewing abnormal traces such as traces $B_1$ and $C_1$ shown in FIG. 7, corrective action can be taken immediately.

The computer encodes or records on a "data disk" the digital information represented by the initial reference traces. In addition, at regular intervals preselected by the operator of the device, the computer also records on the data disk the digital information represented by the live traces displayed on the video monitor. The interval between the recordings is referred to as the "recording time interval" and may be preselected by the operator to be within the range of 1 minute to 60 minutes. The computer is programmed to assure that the recording will be of a full screen of live traces, that is, no recording will be made of partial live traces being generated across the video monitor. Each recording of a full screen of the reference and then live traces is accorded a numerical "file number" and the computer also records on the data disk the time that such recording was made.

At the end of the electrical brain wave monitoring operation, the computer is directed to stop all recording and displays and the data disk is removed from the computer. Information concerning at least the patient and the date are written onto a label on the data disk and the data disk can be stored or filed.

Later on the data disk can be reinserted into the computer and an operator of the device can review all of the information recorded on the data disk. The computer can be directed to display on the terminal a list of the times that the traces were recorded and to display on the video monitor the traces that were recorded at that time in either the high (reference) or low (live) positions.

Hardware

The preferred embodiment of the invention shown in FIG. 1 uses the model 8-16 EEG manufactured by Grass Medical Instruments of Quincy, Mass. While such EEG can accommodate up to 16 separate electrode inputs and provide up to 16 outputs or "channels", in the preferred embodiment of the invention only six voltage-detecting electrodes and six outputs are used.

The specifications for the Grass 8-16 EEG indicate that the normal or "low-level" outputs which are used in the present invention provide an output for each channel of a maximum of 2.8 volts peak to peak, that is, the output for each channel is within the range of $-1.4$ volts to $+1.4$ volts.

The output of the Grass 8-16 EEG must be adjusted to be always in the positive range and the maximum amplitude must be reduced to match with the other components discussed below. These functions can be accomplished by an appropriate conditioning or negative gain amplifier with a simple offset circuit, such as of the type shown in FIG. 3. It will be noted that a separate conditioning amplifier is provided for each channel, the gain of each channel being the same and preferably about 0.5. In the preferred embodiment of the invention, each operational amplifier 20 is a standard "4136" operational amplifier. A single offset circuit 21 is provided with the connection 22 of each separate amplifier circuit having input B, C, D, E or F being connected to the offset as indicated for the amplifier having input A shown toward the top of FIG. 3. The output connections 23 of the amplifiers are connected to the inputs of the A/D convertor as indicated in FIG. 1. The values for the component parts shown in FIG. 3 are as follows:

$C_1 = 2.2$ microfarads
$R_1 = 510$ K ohms
$R_2 = 270$ K ohms
$R_3 = 100$ K ohms (potentiometer)
$R_4 = 100$ K ohms
$R_5 = 11$ K ohms
$R_6 = 100$ ohms (potentiometer)
$R_7 = 75$ ohms In the situation where the gain of each amplifier is 0.5, the $-1.4$ volt to $+1.4$ volt output of the Grass 8-16 EEG is reduced to the range of $-0.7$ volt to $+0.7$ volts. To assure that the output of each conditioning amplifier circuit always is in the positive range, the offset circuit is adjusted to shift the reduced amplitude signal upward about 0.75 volt, putting the output of each conditioning amplifier circuit in the range of about 0.5 volt to about 0.19 volt.

The A/D convertor used in the preferred embodiment of the present invention is the model D+7AI/O manufactured by Cromemco Incorporated of Mountain View, California. The Cromemco convertor has seven different channels, though only six are used in the present invention.

The analog input voltage range to the A/D convertor of 0.5 volt to 0.19 volt used in the preferred embodiment of the present invention produces a digital output from the convertor of about 36 discrete digital points. This matches well with the video monitor used in the preferred embodiment of the present invention which is the Model JB-1201M manufactured by NEC Information Systems Inc. of Lexington, Mass. The vertical resolution of the NEC video monitor is 480 points, allowing 40 points for each of the twelve separate traces that can appear on the video monitor at the same time. Using the 36 digital point output of the Cormemco A/D convertor assures at least 4 point separation between adjacent vertically spaced traces.

In the preferred embodiment of the invention, the A/D convertor is connected to the standard S100 bus of the Horizon microcomputer (Z80 based, 64K random access memory, two 5¼ inch floppy disk drives) manufactured by North Star Computers, Inc. of San Leandro, Calif. Also connected to the computer by way of the bus are a standard S100 clock circuit (preferably the Computerwatch model by Computime of Huntington Beach, Calif.), a graphics controller circuit (preferably the Microangelo model manufactured by Scion Corporation of Vienna, Va., a floating point board circuit (preferably the FPB model manufactured by North Star Computers, Inc. for use with its Horizon computer) and the operator's terminal having both keyboard and a video display (preferably the model IQ120 manufactured by Soroc Technology, Inc. of Anaheim, Calif.). The video monitor is connected to the graphics controller circuit.

Other than a standard 115 volt 60 hertz AC power supply, the only other apparatus required are two standard 5¼ inch floppy disks for the North Star computer. As indicated diagrammatically in FIG. 1, the North Star computer has two slots or disk drives 30 for the two disks. The external program is encoded on one of the disks which is inserted into the first drive and the other disk is inserted into the second drive to be used as the data disk on which information is recorded.

Detailed Operation—Record Mode

The hardware components are connected as discussed above, the external computer program is encoded on a floppy disk which is inserted into the second computer disk drive and a blank data disk is inserted into the computer's first disk drive.

Figure 2:
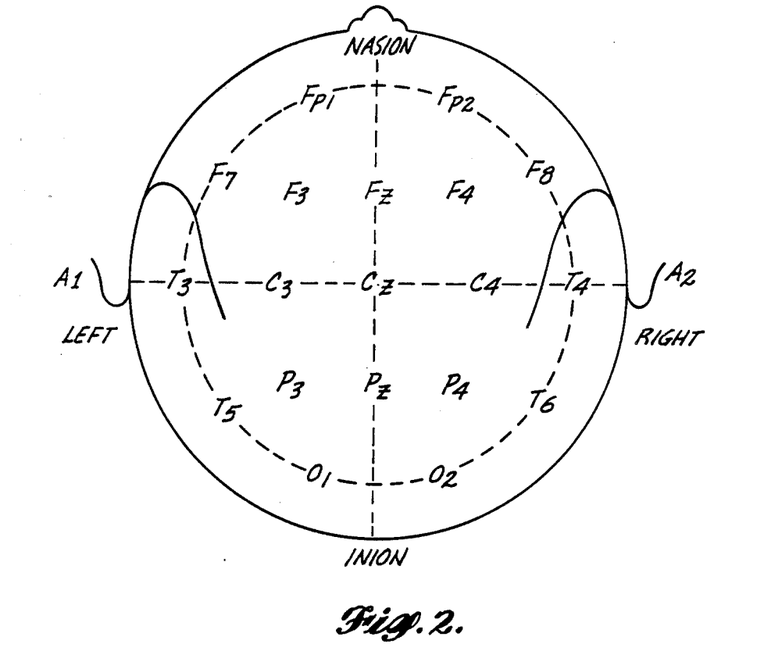
FIG. 2 is a diagrammatic top plan of a human head showing the accepted notations used to indicate EEG electrode placement.

One set of three EEG electrodes is attached to the patient's scalp at each side. Preferably, each electrode is approximately equidistant from the other two electrodes of its set. With reference to FIG. 2, for the electrodes attached at the left side of the scalp, preferably one of them would be attached approximately at the location designated $T_3$ (just above the left ear) with the other two electrodes attached slightly superior to the locations designated $F_7$ and $T_5$, respectively, so that each of the three electrodes is approximately equidistant from the other two electrodes. Similarly, the other three electrodes preferably are attached to the right side of the scalp approximately at location $T_4$ and slightly superior to locations $F_8$ and $T_6$, respectively. The ground electrode 1' of the EEG can be attached at any convenient location such as the patient's forehead. The EEG is adjusted conventionally to provide six variable voltage outputs indicating the voltage differences detected between approximately locations $T_3$-$F_7$, $T_3$-$T_5$, $F_7$-$T_5$, $T_4$-$F_8$, $T_4$-$T_6$ and $F_8$-$T_6$, respectively.

If the data disk is blank and has not been used previously in the device, the operator types "IN2" and, as for all other instructions except as noted below, presses the "RETURN" key of the terminal to indicate that the instruction has been completed. "IN2" stands for "initialize (or format) the disk in slot number 2" which directs the computer to prepare the data disk for receiving information. If the data disk has been used previously, the "IN2" instruction is not necessary.

Next, the operator types GO EEG (RETURN) whereupon the menu of possible instructions to the computer appears on the terminal screen as follows:

Select Activity Please . . . after selection hit RETURN
(A)—Start Recording
(B)—Clear Graphics Screen
(C)—Set Clock
(D)—Reenter a File
(E)—Change Recording Time Interval
(F)—Change Scan Time
To Stop Recording and close file, press S with the CONTROL key
To Record at will, press R with CONTROL
To Update High trace, press U with CONTROL
To Suspend recording, press Z with CONTROL
To Resume recording, press Y with CONTROL
Current Scan factor (____×0.33 secs) is:____
Current recording interval is:____
REF TRACE TIME IS:____

For the initial use of the device, the operator would type C (RETURN) whereupon a series of consecutive instructions appears on the terminal screen for the operator to set the clock circuit of the computer. The clock circuit need only be set once at the initial use of the device and not for subsequent uses.

After the clock has been set, the operator would set the scan time by typing F (RETURN), whereupon instructions appear for setting the scan time. In general, the scan time is calculated as multiples of 0.33 seconds and may be set within the range of about 1 second to about 30 seconds. If, for example, "10" is selected, the scan time will be 10×0.33 seconds or 3.3 seconds. A full trace appearing on the video monitor during operation of the device will represent the output of the A/D convertor over a 3.3 second period.

Next the recording time interval is set by typing E (RETURN), whereupon instructions appear for setting the recording time interval in the range of 1 minute to 60 minutes in 1 minute increments.

Figure 4:
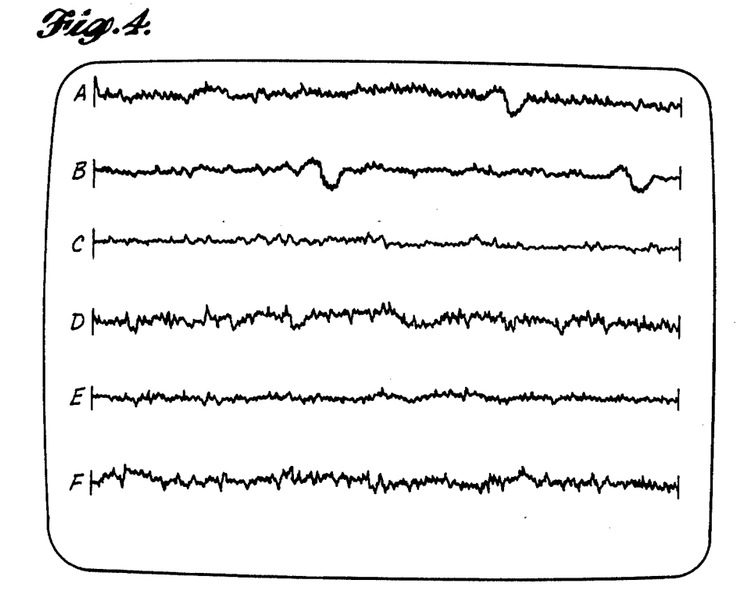
FIGS. 4, 5, 6 and 7 are corresponding diagrammatic illustrations of represenative displays or traces generated by the mechanism of FIG. 1 at different times during its operation.

Then the operator types A (RETURN), whereupon the computer collects and stores the digital output of the A/D convertor for the preselected scan time and displays it on the video monitor as the six reference or high traces A through F as shown in FIG. 4. The reference traces also are recorded on the data disk as the first "file" with the time of recording.

It will be noted that the scan factor selected, the recording interval selected and the time that the reference traces were generated and recorded all appear on the terminal screen along with the menu of instructions.

Figure 7:
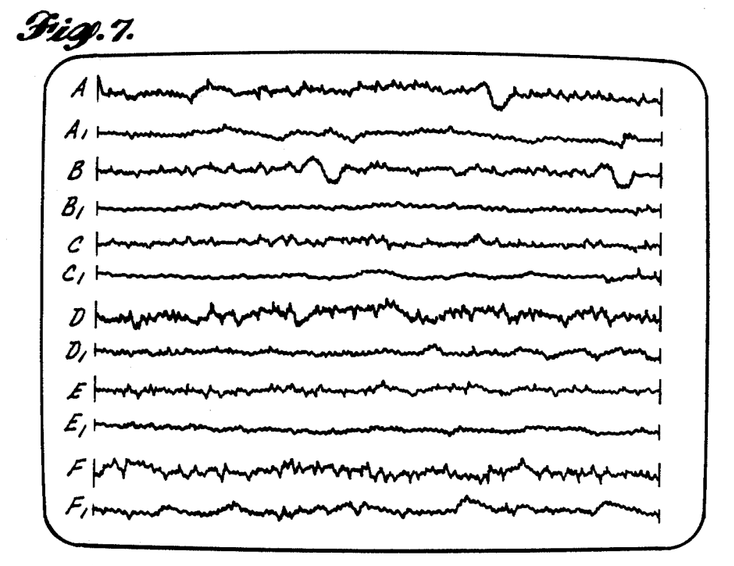

Immediately after displaying the complete reference traces on the video monitor, the computer collects and stores the output of the A/D convertor and then enters it on the video monitor screen with these "live traces" $A_1$ through $F_1$ being displayed directly below the corresponding reference traces as shown in FIGS. 5 through 7. The reference traces continue to be displayed on the monitor screen, but the live traces stay only for about the preselected scan time, whereupon they are erased and new live traces are entered on the screen showing the information received and stored by the computer during the substantially immediately preceding scan time increment.

At each multiple of the preselected recording time interval, the computer waits for a full screen of live traces to be entered on the video monitor and then records it on the data disk as the succeeding file number with the time of recording. About 40 separate files can be recorded on the standard 5¼ inch floppy disk used with the Northstar Horizon computer.

To add an additional recording of the live traces appearing on the monitor screen at any time, the user need only press R and the "CONTROL" key simultaneously, as noted in the menu of instructions. By pressing U and the "CONTROL" key simultaneously, the reference traces are erased and the currently displayed live traces are reproduced as new reference traces that will be preserved on the screen. The automatic recording of information on the data disk can be suspended without altering any other operation of the device by pressing Z and the "CONTROL" key simultaneously (to be resumed by pressing Y and the "CONTROL" key simultaneously). The recording and displaying operation is stopped by pressing S and the "CONTROL" key simultaneously.

At any time, the operator can direct the computer to clear the video monitor screen by pressing B (RETURN), which rarely would be done during the record mode except perhaps while recording has been suspended.

The D (reenter a file) instruction is used when a data disk previously has been used and the operator does not want the computer to record over the files on the beginning of the disk. The computer will jump over the prior recordings as directed by the operator by typing D (RETURN).

As previously noted, at the end of the electrical brain activity monitoring operation, that is, after the operator has directed the computer to "stop recording", the data disk is removed from the computer and the name of the patient and date of recording is written on a label on the data disk.

Detailed Operation—Playback Mode

At any later time, the operator can review any of the information previously recorded on a data disk. The operator inserts the desired disk and types GO PLAYBA (RETURN) whereupon the following menu of possible instructions appears on the display terminal screen:

Select Activity Please . . . after selection hit RETURN
(A)—Show times on disk
(B)—Erase screen
(C)—Display high trace
(D)—Display low trace
Low Trace is:____
High Trace is:____.

Typing A (RETURN) results in a display on the terminal screen of the number of each recorded file along with the time that the file was recorded. Typing C, a desired file number and "RETURN" results in the corresponding traces appearing on the video monitor in the "high" positions (A through F). Typing D, a desired file number and "RETURN" results in the corresponding traces being displayed on the video monitor in the "low" positions ($A_1$ through $F_1$) along with any then appearing traces in the high positions. Either the traces displayed in the high or low positions on the video monitor can be replaced with a different set of recorded traces by the appropriate "C" or "D" instruction. In addition, at any time the video monitor screen can be erased by pressing B (RETURN).

It will be noted that while reviewing the various traces, the operator is informed of which set of traces is being displayed in the high positions and which set of traces is being displayed in the low positions.

Uses, Modifications, Advantages

The preferred electrode locations discussed above are generally over the areas of the brain supplied with blood by the right and left carotid arteries. Such electrode locations are particularly advantageous for monitoring electrical brain activity during surgery on or near one of the carotid arteries. For example, in a surgical operation to alleviate a construction in a carotid artery, such as carotid endarterectomy, typically the artery is clamped at opposite sides of the area to be operated on. Various techniques are used to guard against or to detect cerebral hypoxia during the period that the artery is clamped. A shunt may be used to convey blood past the clamps, but the shunt can interfere with the operation and itself cause complications. More often the intent is to conduct the operation without shunting and other methods are used in an attempt to detect whether cerebral hypoxia is occurring, such as measurement of the stump pressure from the distal internal carotid and/or monitoring electrical brain activity by a conventional EEG. Stump pressure differs for different patients and, although quite commonly used, it is recognized that measurement of stump pressure does not give a reliable indication of whether a specific patient is suffering from cerebral hypoxia. Conventional EEG monitoring is believed to be more reliable, but it is an expensive and complicated procedure which is not always considered justified in view of the short period that the artery must be clamped or the infrequency of complications for the surgical operation to be conducted.

The present invention provides a quick and easy way to evaluate whether a shunt is required. Even if a shunt is used, the effectiveness of the shunt in supplying and continuing to supply blood to the brain can be evaluated quickly and easily. If at any time blood flow to the brain is reduced substantially, such as if the shunt becomes kinked, a decease in the amplitude of electrical brain activity and/or a decrease in high-frequency activity at the side being operated on should be indicated on the video monitor of the present invention. Corrective action can be taken immediately, such as straightening the shunt.

Monitoring electrical brain activity of both sides of the brain even if, for example, only the carotid artery at one side is being operated on can help to pinpoint the cause of a noticed change in electrical brain activity. A decrease in amplitude and/or high-frequency activity for all six live traces may indicate an improper dosage of the anesthetic agent being administered or a malfunction in a respirator resulting in insufficient oxygenation of the blood.

For other types of surgical operations where decreased blood flow may be expected in other areas, different electrode locations can be used.

The automatic periodic recording of the traces during the record mode and the direct comparision of any two sets of traces during the playback mode allow the surgeon or any other person to make a detailed, postoperative study of the patient's electrical brain activity detected during the course of the surgical operation. The indication of the time that each set of traces was recorded allows a comparison with other records kept during the operation. For example, typically the anesthesiologist makes a record of the patient's blood pressure at various times throughout the operation and also makes a record of any changes in the administration of the anesthetic agent. Similarly, the anesthesiology record typically also indicates the time that various stages of the operation were begun and completed. Should a complication arise during or after the surgical operation, the postoperative evaluation of electrical brain activity permitted by the present invention may be very helpful in identifying the cause of the complication, or at least in eliminating one or more possible causes.

As compared to a surgical operation conducted without any monitoring of electrical brain activity, the present invention provides a valuable source of information which otherwise would not be available.

As compared to an operation conducted with electrical brain activity monitored by a conventional EEG, the present invention still provides localized, specific information on a patient's electrical brain activity, but in a form that can be evaluated by a skilled technician or the anesthesiologist without requiring an experienced EEG specialist for such evaluation. In addition, a direct comparison can be made of the previously taken reference traces and the juxtaposed more recent live traces, whereas such an arrangement of traces is not provided in a conventional EEG chart output. Further, a permanent record is available for postoperative evaluation, but in a compact form that can be evaluated quickly and easily, witout necessarily requiring an experienced EEG specialist.

As compared to an operation conducted with electrical brain activity monitored by a modified EEG-type device such as the Maynard cerebral function monitor, the present invention provides traces indicating both amplitude and frequency of electrical brain activity at several distinct locations, rather than a single overall indication of electrical brain activity showing only amplitude as provided by the Maynard device.

We claim:

1. In mechanism for monitoring electrical brain activity of a patient during a medical procedure including means for detecting the electrical brain activity, the improvement comprising the combination of an electronic video monitor, and means for simultaneously displaying on said monitor in juxtaposed relationship a reference trace indicating electrical brain activity of the patient during a selected reference portion of such procedure and a separate first current trace indicating electrical brain activity of the patient during a subsequent portion of such procedure, said displaying means including means for displaying a separate second current trace on said video monitor in juxtaposed relationship to said reference trace and indicating electrical brain activity of the patient during a portion of the procedure subsequent to the portion represented by said first current trace, and for replacing said first current trace with said second current trace, while continuing to display said reference trace on said video monitor and while the procedure continues.

2. In mechanism for monitoring electrical brain activity of a patient during a medical procedure including means for detecting the electrical brain activity, the improvement comprising an electronic video monitor, and means for continuously displaying on said video monitor in juxtaposed relationship a reference trace indicating electrical brain activity of the patient during a selected reference portion of such procedure and at least one of a series of consecutive separate current traces each indicating the patient's electrical brain activity during the immediately preceding portion of such procedure while such procedure continues, said displaying means including means for replacing one of said current traces with another while maintaining said reference trace on said monitor.

3. In the mechanism defined in claim 2, means enabling adjustment of the length of the immediately preceding portion of the procedure represented by each current trace.

4. In the mechanism defined in claim 2, means for automatically recording the most recent current trace at preselected intervals.

5. In the mechanism defined in claim 4, the detecting means including means for providing an analog electrical signal of electrical brain activity of the patient, the displaying means including means for converting said analog signal to a digital signal of the electrical brain activity, and the recording means including means for recording the digital signal.

6. Mechanism for monitoring electrical brain activity of a patient during a medical procedure comprising means for continuously detecting electrical brain activity of the patient during such procedure, means for continuously generating a digital signal of such electrical brain activity as such activity is detected, a computer having a memory, means for continuously storing said digital signal in said memory of said computer as said digital signal is produced, an electronic video monitor having a screen, means for displaying on said screen a reference trace indicating electrical brain activity of the patient during a selected reference portion of the procedure, and means for automatically at preselected intervals recalling the most recent portion of said digital signal stored in said memory of said computer and for immediately using said recalled portion to produce a current trace on said screen of said electronic video monitor so as to indicate in viewable form the electrical brain activity represented by said most recent portion of said signal while the medical procedure continues and while continuing to detect electrical brain activity of the patient, said displaying and recalling means including means for replacing one current trace with a more recent current trace while maintaining the display of said reference trace.

7. In the mechanism defined in claim 6, means for automatically and at uniformly spaced preselected intervals recording the most recent portion of the digital signal while the medical procedure continues so as to create a record of uniformly spaced portions of the digital signal.

8. In the mechanism defined in claim 7, means enabling adjustment of the interval between consecutive recordings.

9. The method of monitoring electrical brain activity of a patient during a medical procedure which comprises continuously detecting electrical brain activity of the patient during such procedure, continuously generating a digital signal of such electrical brain activity as such activity is detected, continuously storing the digital signal in the memory of a computer as the digital signal is produced, displaying on the screen of an electronic video monitor a reference trace indicating electrical brain activity of the patient during a selected reference portion of such procedure, automatically at preselected intervals recalling the most recent portion of the digital signal stored in the memory of the computer and immediately using such recalled portion to produce a current trace on the screen of the monitor while maintaining the display of the reference trace so as to indicate in viewable form the electrical brain activity represented by such reference and current traces while the medical procedure continues and while continuing to detect electrical brain activity of the patient, and including subsequently replacing the current trace with a more recent current trace while continuing to maintain the display of the reference trace.

10. In the method defined in claim 9, the improvement which further comprises automatically and at uniformly spaced preselected intervals recording in magnetic media the most recent portion of the digital signal while the medical procedure continues so as to create a record of uniformly spaced portions of the digital signal.

11. The method of monitoring electrical brain activity of a patient during a medical procedure which comprises detecting electrical brain activity of the patient during a selected first portion of such procedure, generating a first digital signal of the electrical brain activity detected during such first portion, using the first digital signal to produce a display of a first trace on the screen of an electronic video monitor so as to indicate in viewable form the electrical brain activity detected during such first portion, maintaining the display of the first trace on the screen of the electronic video monitor, detecting electrical brain activity of the patient during a selected second portion of such procedure subsequent to the first portion, generating a second digital signal of the electrical brain activity detected during such second portion, using such second digital signal to produce a second trace on the screen of the electronic video monitor in juxtaposed relationship to the first trace so as to indicate in viewable form the electrical brain activity detected during such second portion for enabling visual comparison of the first and second traces while the medical procedure continues and while continuing to detect electrical brain activity of the patient, detecting electrical brain activity of the patient during a selected third portion of such procedure subsequent to the second portion, generating a third digital signal of the electrical brain activity detected during such third portion, erasing the second trace, and using the third digital signal to produce a third trace on the screen of the electronic video monitor in replacement of the second trace and while maintaining the display of the first trace with the first and third traces in juxtaposed relationship so as to indicate in viewable form the electrial brain activity detected during such third portion for enabling visual comparison of the first and third traces while the medical procedure continues and while continuing to detect electrical brain activity of the patient.

12. A method of monitoring electrical brain activity of a patient during a medical procedure which comprises continuously detecting electrical brain activity of the patient, continuously generating an electrical signal of such electrical brain activity, using the electrical signal to produce a display of a reference trace on the screen of an electronic video monitor indicating the electrical brain activity of the patient detected during a selected reference portion of such procedure, and, while preserving the display of the reference trace on the screen of the electronic video monitor, continuously using the electrical signal to produce a display of a separate live trace on the screen of the electronic video monitor in juxtaposed relationship to the reference trace and indicating current brain activity of the patient for enabling visual comparison of the two traces to detect discrepancies while the medical procedure continues by continuously generating a digital signal of the electrical brain activity, storing the digital signal in the memory of a computer as the digital signal is produced, and automatically at preselected intervals recalling from the memoy of the computer the most recently stored portion of the digital signal indicating current electrical brain activity, immediately using such recalled signal to produce a display of the separate live trace on the screen of the electronic video monitor in juxtaposed relationship to the reference trace, maintaining the display of the separate live trace for a preselected period of time while continuing to store the digital signal in the memory of the computer as the digital signal continues to be produced, and, immediately following such preselected period of time, recalling from the memory of the computer the next portion of the digital signal indicating current electrical brain activity, erasing the display of the previously produced separate live trace and immediately using such next recalled portion of the digital signal to produce a new separate live trace on the screen of the electronic video monitor in juxtaposed relationship to the reference trace.

13. The method defined in claim 12, including automatically and at uniformly spaced preselected intervals recording in magnetic media the most recent portion of the digital signal while the medical procedure continues so as to create a record of uniformly spaced portions of the digital signal.

14. The method defined in claim 12, including continuously detecting electrical brain activity of the patient at a plurality of different areas of the patient's head, continuously generating a separate electrical signal of such electrical brain activity detected at each such separate area, using the separate electrical signals to produce a plurality of reference traces indicating, respectively, the electrical brain activity detected during the selected reference portion at such different areas, and, while preserving the displays of the reference traces, continuously using the separate electrical signals to produce displays of separate live traces in juxtaposed relationship to the corresponding reference traces and indicating current brain activity of the patient for enabling visual comparison of the reference and corresponding live traces to detect discrepancies while the medical procedure continues.

* * * * *